(12) United States Patent
Mingozzi et al.

(10) Patent No.: US 7,108,697 B2
(45) Date of Patent: Sep. 19, 2006

(54) STABILIZING SUPPORT FOR OPENING- AND CLOSING-WEDGE OSTEOTOMIES

(75) Inventors: Franco Mingozzi, Lippo Di Calderara (IT); Alan Dovesi, Bologna (IT)

(73) Assignee: Citieffe S.R.L., Calderara Di Reno (IT)

( * ) Notice: Subject to any disclaimer, the term of this patent is extended or adjusted under 35 U.S.C. 154(b) by 444 days.

(21) Appl. No.: 10/390,732

(22) Filed: Mar. 19, 2003

(65) Prior Publication Data

US 2003/0199875 A1    Oct. 23, 2003

(30) Foreign Application Priority Data

Apr. 23, 2002   (IT)   ............... BO2002A0224

(51) Int. Cl.
   *A61B 17/58*   (2006.01)
(52) U.S. Cl. ................................................ 606/69
(58) Field of Classification Search ............... 606/69, 606/70, 71
   See application file for complete search history.

(56) References Cited

U.S. PATENT DOCUMENTS

| | | | |
|---|---|---|---|
| 3,741,205 A * | 6/1973 | Markolf et al. ............... 606/69 |
| 4,651,724 A * | 3/1987 | Berentey et al. .............. 606/69 |
| 5,662,655 A | 9/1997 | Laboureau et al. | |
| 5,779,706 A * | 7/1998 | Tschakaloff .................. 606/69 |
| 5,827,286 A * | 10/1998 | Incavo et al. ................. 606/71 |
| 5,921,988 A | 7/1999 | Legrand | |
| 6,168,596 B1 * | 1/2001 | Wellisz et al. ................ 606/69 |
| 6,524,311 B1 * | 2/2003 | Gaines, Jr. ................... 606/61 |
| 2004/0092929 A1 * | 5/2004 | Zindrick ....................... 606/61 |
| 2004/0162558 A1 * | 8/2004 | Hegde et al. ................. 606/61 |

FOREIGN PATENT DOCUMENTS

| | | |
|---|---|---|
| DE | 202 04513 | 8/2002 |
| FR | 2 668 921 | 5/1992 |
| FR | 2 709 410 | 3/1995 |
| FR | 2 764 183 | 12/1998 |

\* cited by examiner

*Primary Examiner*—Eduardo C. Robert
*Assistant Examiner*—James L Swiger
(74) *Attorney, Agent, or Firm*—Modiano & Associati; Albert Josif; Daniel J. O'Byrne

(57) ABSTRACT

A stabilizing support for opening- and closing-wedge osteotomies, constituted by a plate for connecting, by screws, two bone portions formed by an osteotomy rima; the plate comprises fixing means that are adapted to be inserted and fixed in each one of the portions in order to lock the portions in a preset configuration, so as to support an axial load that bears on the bone.

5 Claims, 2 Drawing Sheets

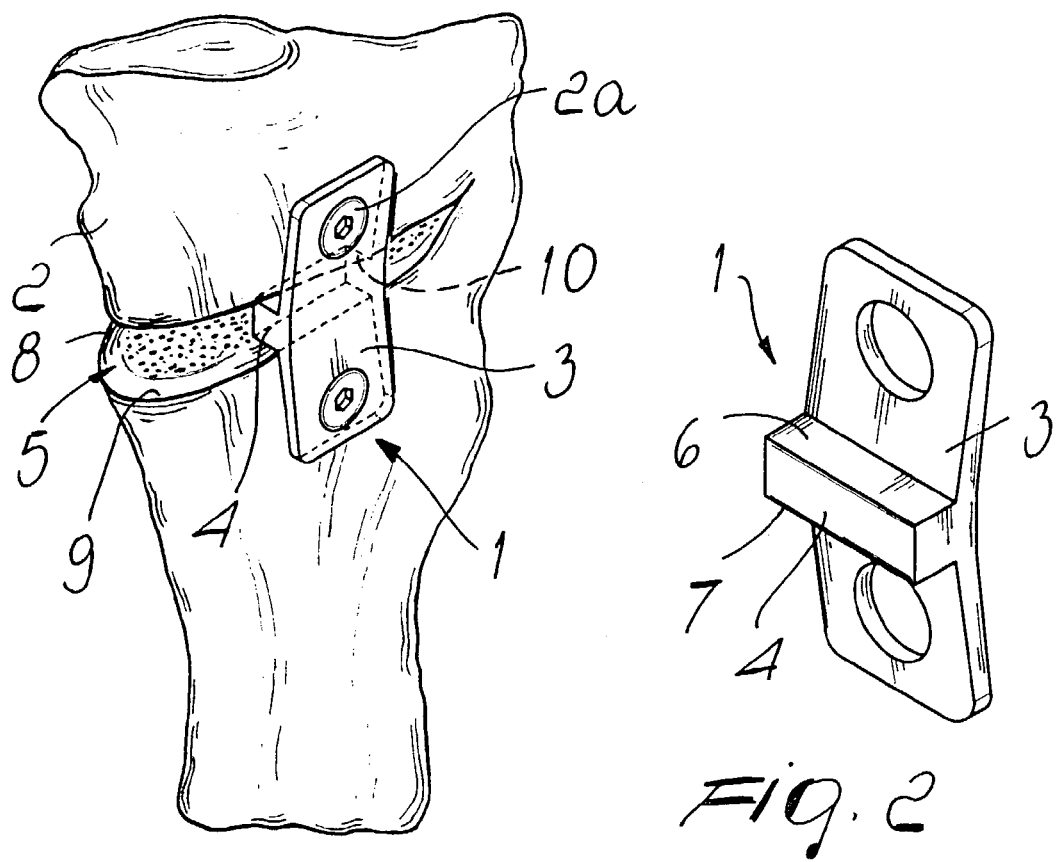
Fig. 1 (PRIOR ART)
Fig. 2 (PRIOR ART)
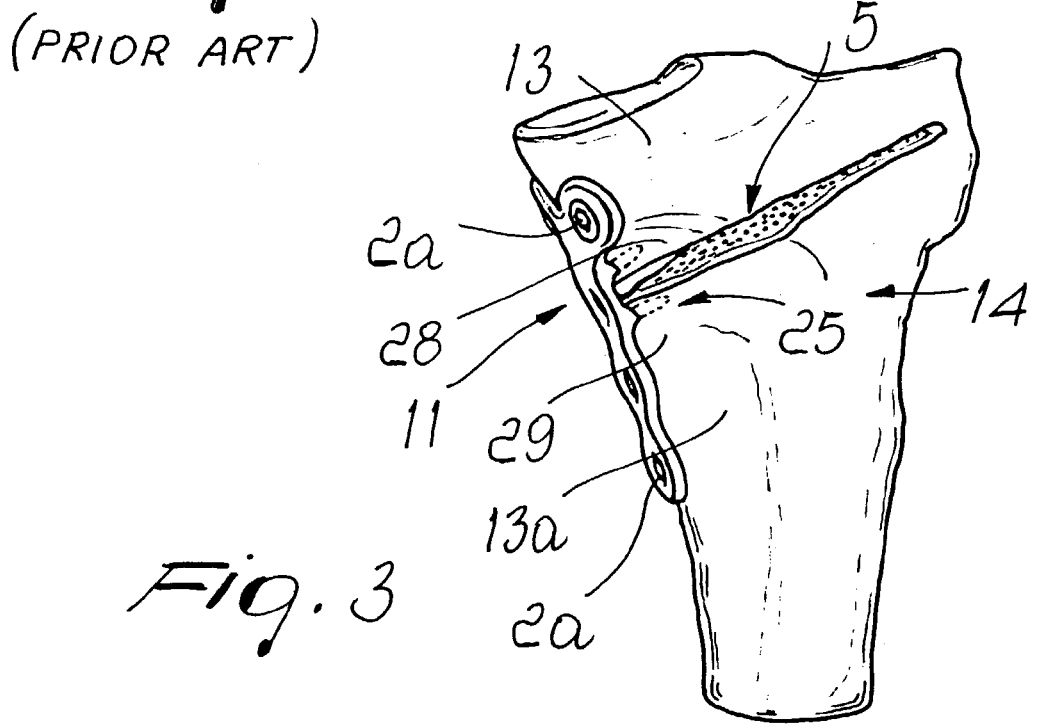
Fig. 3

STABILIZING SUPPORT FOR OPENING- AND CLOSING-WEDGE OSTEOTOMIES

BACKGROUND OF THE INVENTION

The present invention relates to a stabilizing support for opening- and closing-wedge osteotomies, particularly of the miniinvasive type for tibial and femoral osteotomies.

The practice of osteotomy, performed in particular at the distal epiphysis of the femur or at the proximal epiphysis of the tibia in order to modify the load conditions of the knee, is currently widely used and often is the most advisable solution when the patient's angle between the diaphyseal longitudinal axis of the femur and the longitudinal axis of the tibia is open medially or laterally at values that differ from those considered anatomically normal.

Stabilizing supports constituted by a plate for connecting, by means of screws, the two bone portions formed by the osteotomy rima are known. For better comprehension, reference should be made to FIGS. 1 and 2, which refer to a particular stabilizing support, disclosed in U.S. Pat. Nos. 5,620,448 and 5,749,875.

FIG. 1 is a perspective view of a detail of a stabilizing support 1 fixed to the proximal epiphysis of the tibia 2 by means of screws 2a and constituted by a plate 3 provided with a tooth 4 to be inserted in a osteotomy rima 5; such tooth, which has an upper face 6 and a lower face 7, is suitable to support the axial load that bears on the bone. FIG. 2 is instead a perspective view of such support.

Support 1 has a drawback linked to the shape of the tooth 4, which is preferably parallelepipedal and therefore does not ensure correct resting of opposite surfaces 8 and 9 formed by the rima 5, which is substantially wedge-shaped. The contact between the surfaces 8 and 9 and the tooth 4 in fact occurs only along points or segments (for example along the segment 10) and therefore is not distributed correctly on the upper face 6 and the lower face 7 of the tooth 4.

Accordingly, the screws 2a are loaded excessively by the weight of the body of the patient, causing wear and mechanical instability. Furthermore, the presence of the tooth 4 inserted in the osteotomy rima 5 prevents its correct and complete filling with any bone inserts; therefore, after the removal of the support, the bone portion affected by the rima might not be perfectly intact and might have insufficient mechanical strength.

SUMMARY OF THE INVENTION

The aim of the present invention is to obviate the cited drawback by providing a stabilizing support that allows to achieve effective locking and lo support of the two bone portions formed by an osteotomy rima according to a preset configuration and at the appropriate angle.

Within this aim, an object of the present invention is to provide a stabilizing support that is easy to apply and is versatile for both opening- and closing-wedge osteotomies.

Another object of the present invention is to provide a stabilizing support that ensures optimum filling of the osteotomy rima with a bone insert and allows to obtain an intact and mechanically strong bone.

Another object of the present invention is to provide a stabilizing support with a structure that is simple, relatively easy to provide in practice, safe in use, effective in operation, and at a relatively low cost.

This aim and these and other objects that will become better apparent hereinafter, are achieved by the present stabilizing support for opening- and closing-wedge osteotomies, constituted by a plate for connecting, by means of screws, two bone portions formed by an osteotomy rima, characterized in that said plate comprises fixing means that are adapted to be inserted and fixed in each one of said portions in order to mutually lock said portions in a preset configuration; so as to support an axial load that bears on said bone.

BRIEF DESCRIPTION OF THE DRAWINGS

Further characteristics and advantages of the present invention will become better apparent from the detailed description of a preferred but not exclusive embodiment of a stabilizing support for opening- and closing-wedge osteotomies according to the invention, illustrated only by way of non-limitative example in the accompanying drawings, wherein:

FIG. 1 is a perspective view of a detail of a stabilizing support according to the prior art;

FIG. 2 is a perspective view of a detail of the support of FIG. 1.

FIG. 3 is a detail perspective view of the stabilizing support according to the invention, applied to the proximal epiphysis of the tibia;

DESCRIPTION OF THE PREFERRED EMBODIMENTS

Figure 4:
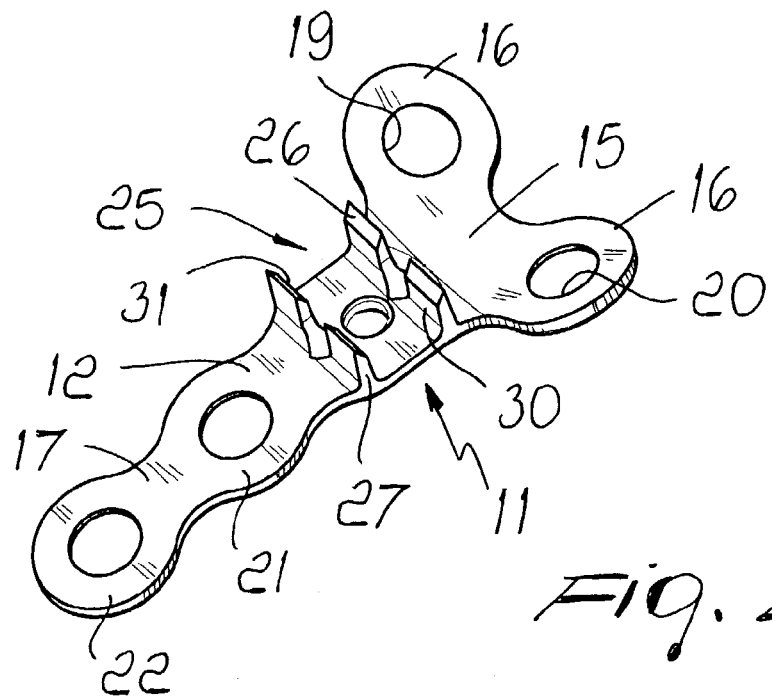
FIG. 4 is a perspective view of the support of the present invention.
Figure 6:
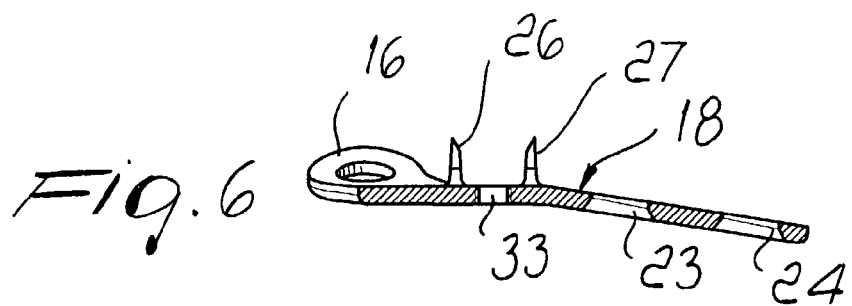
FIG. 6 is a longitudinal sectional view of the support of the invention, taken along the line VI—VI of FIG. 5.
Figures 5, 7:
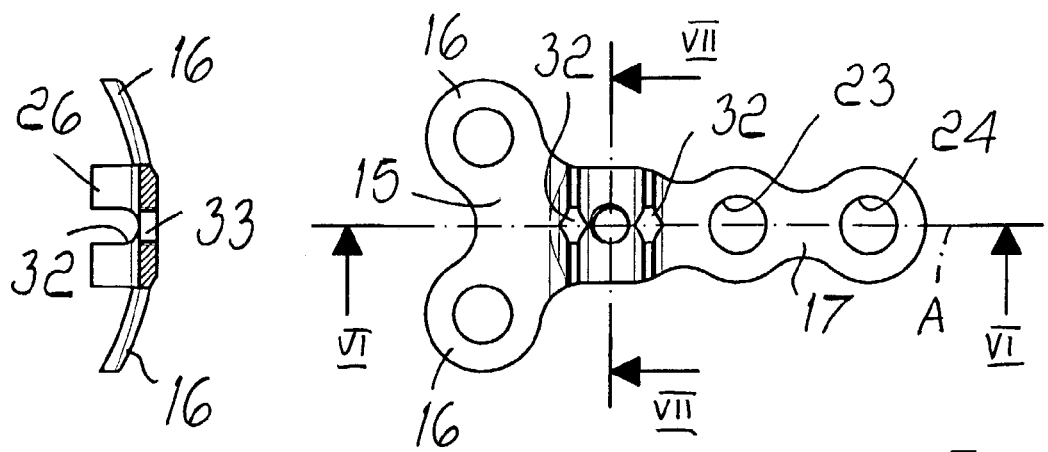
FIG. 5 is a front view of the support of the invention.
FIG. 7 is a transverse sectional view of the support of the invention, taken along the line VII—VII of FIG. 5.

With reference to the figures, the reference numeral 11 generally designates a stabilizing support for opening- and closing-wedge osteotomies according to the invention.

The support, which is of the miniinvasive type particularly usable for tibial and femoral osteotomies that entail forming an osteotomy rima 5 in the distal epiphysis of the femur or in the proximal epiphysis of the tibia, is constituted by a plate 12 for connecting, by means of screws 2a, the two portions 13, 13a of bone 14 formed by said rima 5.

The plate 12 preferably has a low thickness and a longitudinal plane of symmetry A, and has a first end 15, which is formed by two lobes 16 that are arranged mirror-symmetrically with respect to the plane of symmetry A, and a second end 17, which is substantially elongated. The lobes 16 are slightly curved with respect to the front plane of the plate 12, so as to define, on the inner face 18 of the plate, a concavity that substantially corresponds to the anatomical curvature of the surface of the epiphysis of the bone 14 on which the osteotomy has been performed; the lobes 16 are affected respectively by a first circular eye 19 and by a second circular eye 20 for the passage of the screws 2a to be inserted in the bone 14.

The second end 17 of the plate 12 forms, with respect to the first end 15, an angle that is suitable to facilitate the application of the plate to the osteotomy rima 5, adapting to the anatomical shape of the epiphysis of the bone 14, and has a shape that forms two expansions 21 and 22 that are aligned and in which there are third and fourth circular eyes 23, 24 for the passage of the screws 2a; the axes of the eyes belong to the longitudinal plane of symmetry A of the plate 12.

According to the invention, the plate 12 comprises fixing means 25, which are suitable to be inserted and fixed in each one of the two portions 13, 13a formed by the osteotomy rima 5, in order to lock said portions in a preset configuration, so as to withstand the axial load that bears on the bone 14.

The fixing means 25 comprise a first protrusion 26 and a second protrusion 27, which are parallel and face each other and protrude from the inner face 18 of the plate 12 and are designed to be inserted and fixed in the portions 13, 13a of the bone 14 respectively at the upper edge 28 and at the lower edge 29 of the osteotomy rima 5.

The first protrusion 26 and the second protrusion 27 are substantially shaped like a sharp tooth, with respective facing tapering walls 30 and 31; each one of the protrusions is further provided with a respective central notch 32 that is substantially U-shaped.

A threaded through hole 33 is provided in the portion of the plate 12 that lies between the first protrusion 26 and the second protrusion 27 in order to detachably fix means for inserting and fixing the protrusions 26 and 27 in the respective portions 13 and 13a of the bone, said means being suitable to apply a pressure that drives said protrusions into the bone 14.

The method of use of the stabilizing support according to the invention is as follows: after providing the osteotomy rima 5 on the affected bone 14, for example on the distal epiphysis of the femur or on the proximal epiphysis of the tibia, the angle at which the two portions 13, 13a of bone 14 must be arranged to obtain correct load conditions on the knee is determined by means of suitable instruments.

Then the first protrusion 26 and the second protrusion 27 are inserted and fixed respectively at the upper and lower edges 28 and 29 of the osteotomy rime 5, fixing the plate 12 to the portions 13, 13a of bone by means of corresponding screws 2a.

The support according to the invention allows to lock effectively, in a preset configuration, the portions 13, 13a of bone formed by an osteotomy rima 5, so as to support the axial load that bears on the bone 14 without subjecting the screws 2a to excessive stress; the support also ensures flexible and versatile use both for opening-wedge osteotomies and for closing-wedge is osteotomies.

The complete absence of parts of the support arranged inside the osteotomy rima 5 leads to reduced invasiveness, which allows perfect filling of the rima with any bone inserts and therefore returns, after removal, a bone portion that is intact and mechanically strong.

It has thus been shown that the invention achieves the intended aim and objects.

The invention thus conceived is susceptible of numerous modifications and variations, all of which are within the scope of the appended claims.

All the details may further be replaced with other technically equivalent ones.

In practice, the materials used, as well as the shapes and dimensions, may be any according to requirements without thereby abandoning the scope of the protection of the appended claims.

The disclosures in Italian Patent Application No. B02002A000224 from which this application claims priority are incorporated herein by reference.

What is claimed is:

1. A stabilizing support for opening- and closing-wedge osteotomies, constituted by a plate and screws for connecting two portions of bone formed by an osteotomy rima, said plate having a longitudinal extension which extends between a first end of said plate and a second end of said plate, passages being provided at said first and second ends for passing said screws therethrough for connecting said plate to the two portions of the bone, said plate further comprising fixing means that are adapted to be inserted and fixed in each one of said portions in order to lock said portions in a preset configuration, so as to support an axial load that bears on said bone, said fixing means comprising a first protrusion and a second protrusion, which are parallel and face each other in a direction of said longitudinal extension and protrude at right angles from an inner face of said plate for being inserted and fixed in said portions respectively at an upper edge and at a lower edge of said rima, said first and second protrusions being wedge-shaped, with respective tapering walls that face each other, and said first and second protrusions both being arranged between said passages of said first and second ends of said plate with respect to said longitudinal extension of said plate; wherein said first and second protrusions are each provided centrally with a respective notch that is U-shaped in a transverse direction substantially perpendicular to said longitudinal extension of said plate.

2. The stabilizing support according to claim 1, wherein said plate is affected, in a portion that lies between said first and second protrusions, by a threaded hole for the detachable fixing of means for inserting and fixing said first and second protrusions in said portions of bone.

3. The stabilizing support according to claim 1, wherein said first end of said plate is constituted by two lobes, which are arranged mirror-symmetrically with respect to a longitudinal plane of symmetry of said plate, said lobes being affected respectively by a first eye and a second eye of said passages for the passage of said screws.

4. The stabilizing support according to claim 3, wherein said lobes are curved with respect to a front plane of said plate so as to form, on said inner face, a concavity that corresponds substantially to the anatomical curvature of the surface of the epiphysis of said bone.

5. The stabilizing support according to claim 3, wherein said second end of said plate has a third eye and a fourth eye of said passages for the passage of said screws, whose respective axes belong to said longitudinal plane of symmetry.

* * * * *